United States Patent [19]

Mattone et al.

[11] 4,178,287
[45] Dec. 11, 1979

[54] PROCESS FOR THE PURIFICATION OF CAPROLACTAM BY MEANS OF OZONE

[75] Inventors: Roberto Mattone, Frascati; Mario Catoni, Colleferro, both of Italy

[73] Assignee: SNIA Viscosa Societa Nazionale Industria Applicazioni Viscosa S.p.A., Italy

[21] Appl. No.: 968,807

[22] Filed: Dec. 12, 1978

Related U.S. Application Data

[63] Continuation of Ser. No. 782,092, Mar. 28, 1977, abandoned.

[30] Foreign Application Priority Data

Apr. 9, 1976 [IT] Italy .............................. 22108 A/76

[51] Int. Cl.$^2$ .......................................... C07D 201/16
[52] U.S. Cl. .............................................. 260/239.3 A
[58] Field of Search ................................ 260/239.3 A

[56] References Cited

U.S. PATENT DOCUMENTS

| | | | |
|---|---|---|---|
| 2,752,336 | 6/1956 | Boon et al. | 260/239.3 A |
| 3,600,381 | 8/1971 | Yamamoto et al. | 260/239.3 A |

*Primary Examiner*—Alan L. Rotman
*Assistant Examiner*—Robert T. Bond
*Attorney, Agent, or Firm*—Wenderoth, Lind & Ponack

[57] ABSTRACT

There is described a process for the purification of caprolactam from the oxidable impurities present therein, by means of a treatment with an oxidizing agent consisting of ozone, the process comprising the steps of dissolving the polluted caprolactam into a solvent inert to ozone, such as water, and of causing the ozone to bubble through the resulting solution, the concentration of the caprolactam in the solution being preferably comprised between about 40% and 78% by weight of caprolactam, and the treatment being preferably effected at a temperature between the freezing temperature of the solution and 70° C.

5 Claims, No Drawings

PROCESS FOR THE PURIFICATION OF CAPROLACTAM BY MEANS OF OZONE

This is a continuation of application Ser. No. 782,092, filed Mar. 28, 1977, now abandoned.

The present invention refers to a process for the purification of caprolactam by means of ozone.

It is known to purify caprolactam from oxidizable impurities by treatment with an oxidizing agent such as potassium permanganate. Said process however is particularly burdensome both from the economical and from the operative viewpoint, since it involves:

(a) the necessity of dosing a solid, which involves difficulties depending on the crystalline form of the salt;

(b) the necessity of filtering the manganese dioxide formed, after adding kieselguhr; the filter cake, besides costituting one of the vehicles of caprolactam losses, is also a problem from the waste discharge viewpoint.

The applicant has now surprisingly found that by substituting permanganate with ozone, it is possible to active a very efficient purification of caprolactam, said process being free from the drawbacks inherent in the known processes.

The object of the present invention is therefore a process for the purification of caprolactam form the oxidizable impurities present therein, by means of a treatment with an oxidizing agent, characterized by the fact that said oxidizing agent is ozone.

According to a preferred embodiment of the process which is the object of the present invention, the caprolactam polluted by oxidizable impurities, is firstly dissolved in a suitable solvent, and subsequently ozone is bubbled through the resulting solution.

Any solvent inert to ozone, for instance water, is suitable for use in the process.

The caprolactam can be treated with ozone either in a concentrated or in a diluted solution. Preferably the concentration of the caprolactam in the solution is comprised between about 40% and 78% by weight of caprolactam, such concentration range not being limitative as it is not critical with regard to the operability or, more properly, the reaction mechanism of the process, but is only suggested for economical reasons. It is generally preferable to operate at the maximum concentration permitted by the solubility of caprolactam at the process temperatures.

The ozone employed as oxidizing agent may be contained in oxygen, in air, in air diluted with nitrogen or in any other gaseous mixture.

The limits of the concentration of ozone in air depend on the particular system used for producing $O_3$ and are therefore dictated above all by technological considerations. Preferably said concentrations are maintained below 30 mg of ozone per liter, more preferably between 8 and 30 mg/liter.

According to the present invention, the treatment of the caprolactam solution with ozone is effected at a temperature conveniently comprised between the freezing temperature of the solution and 70° C., preferably between 20° and 50° C.; and such treatment may be effected either at atmospheric pressure or under or super-atmospheric pressure or even under a moderate aspiration.

Preferably, according to the present invention, an ozone caprolactam ratio comprised between 150 and 1500 mg of ozone per kg of caprolactam is absorbed during the treatment, the specific amount depending on the amount of the impurities present in the raw caprolactam.

The following examples are illustrative but not limitative.

EXAMPLE 1

500 gr of an 78% by weight aqueous caprolactam solution is introduced into a flask provided with a stirrer.

An oxygen stream, containing 0.08 gr/lt of ozone, is bubbled through said solution at room temperature for a period of one hour, at a rate of 10 lt/hr, whereby an amount of ozone equal to 0.09% by weight of the caprolactam is absorbed.

After said treatment with ozone, the caprolactam containing solution is subjected to a first rectification with the elimination of 5% by weight of head fractions to a second rectification with the elimination of 20% by weight of tail fractions, whereby a fraction is isolated which consists of a caprolactam having a permanganate number of about 3000 (measured according to the norm for caprolactam of UNICHIM Italiana).

The same caprolactam not treated with ozone but only subjected to the said two rectifications, has permanganate number equal to 0.

EXAMPLE 2

By proceeding as described in example 1, but bubbling the ozone containing oxygen through the caprolactam solution for a period of 2 hours, an amount of ozone equal to 0.11% by weight of the caprolactam is absorbed. The product, after being subjected to the rectifications as described in example 1, is found to have a permanganate number equal to 9000.

We claim:

1. In a process for the purification of caprolactam from oxidizable impurities present therein, by treatment with an oxidizing agent, the improvement which comprises dissolving caprolactam containing oxidizable impurities in water to form an aqueous solution and contacting said aqueous solution with ozone as said oxidizing agent, the ozone:caprolactam ratio being between about 150 to 1500 milligrams of ozone per kilogram of caprolactam.

2. The process according to claim 1 wherein an ozone-air mixture is employed as the source of ozone, said mixture having a concentration of between about 8 and 30 milligrams of ozone per liter.

3. Process according to claim 1, wherein the concentration of the concentration of the caprolactam in said aqueous solution is between about 40% and 78% by weight.

4. Process according to claim 1, wherein said contacting with ozone is effected at a temperature between the freezing temperature of the solution and 70° C.

5. Process according to claim 4 wherein said contacting with ozone is effected at a temperature between about 20° and 50° C.

* * * * *